United States Patent
Fornasari et al.

[11] Patent Number: 6,084,045
[45] Date of Patent: *Jul. 4, 2000

[54] CATIONIC POLYMER

[75] Inventors: Giancarlo Fornasari, Pescara; Alessandro Gagliardini, Jesi, both of Italy

[73] Assignee: The Procter & Gamble Company, Cincinnati, Ohio

[ * ] Notice: This patent issued on a continued prosecution application filed under 37 CFR 1.53(d), and is subject to the twenty year patent term provisions of 35 U.S.C. 154(a)(2).

[21] Appl. No.: 08/836,122
[22] PCT Filed: Nov. 13, 1995
[86] PCT No.: PCT/US95/14676
§ 371 Date: May 12, 1997
§ 102(e) Date: May 12, 1997
[87] PCT Pub. No.: WO96/15162
PCT Pub. Date: May 23, 1996

[30] Foreign Application Priority Data

Nov. 10, 1994 [IT] Italy ................ TO94A0888

[51] Int. Cl.[7] ................ C08L 130/06
[52] U.S. Cl. ............ 526/239; 526/277; 526/287; 526/295; 526/310
[58] Field of Search ............ 526/295, 277, 526/239, 287, 310

[56] References Cited

U.S. PATENT DOCUMENTS

| | | | |
|---|---|---|---|
| 3,879,447 | 4/1975 | Samour et al. | 260/482 R |
| 3,968,037 | 7/1976 | Morgan et al. | 210/47 |
| 4,151,202 | 4/1979 | Hunter et al. | 526/295 |
| 4,225,445 | 9/1980 | Dixon | 526/295 |
| 4,654,378 | 3/1987 | Hunter et al. | 526/295 |
| 4,686,066 | 8/1987 | Hofinger et al. | 526/295 |
| 4,742,134 | 5/1988 | Butler et al. | 526/295 |
| 5,330,656 | 7/1994 | Hassick | 210/708 |
| 5,422,408 | 6/1995 | Cramm et al. | 526/295 |
| 5,597,858 | 1/1997 | Ramesh et al. | 526/295 |

FOREIGN PATENT DOCUMENTS

| | | | |
|---|---|---|---|
| 0103698 | 3/1984 | European Pat. Off. | 526/295 |
| 0161762 | 11/1985 | European Pat. Off. | 526/295 |
| 0161763 | 11/1985 | European Pat. Off. | 526/295 |
| 61-126114 | 6/1986 | Japan | 526/295 |
| 0965493 | 7/1964 | United Kingdom | 526/295 |

*Primary Examiner*—Bernard Lipman
*Attorney, Agent, or Firm*—Carl J. Roof; Mary Catherine Hentz; Edward J. Milbrada

[57] ABSTRACT

The invention provides a water swellable, water-insoluble polymer comprising units derived from a diallylic quaternary ammonium salt monomer cross-linked by a suitable polyfunctional vinyl compound, at least a substantial proportion of the function groups being in basic form. The invention also provides a process for the production of a water-swellable, water-insoluble polymer which comprises polymerising a diallylic quaternary ammonium salt monomer and a suitable polyfunctional vinyl compound as cross-linking agent by cationic polymerisation in an aqueous phase using a free radical catalyst and polymers obtainable thereby. The water absorbent polymers are superabsorbents having improved water absorption properties particularly in respect of saliva solution.

23 Claims, No Drawings

CATIONIC POLYMER

The present invention relates to a cationic polymer more particularly a water absorbent polymer of the type commonly referred to as a "superabsorbent".

The substances currently termed "superabsorbents" are typically slightly cross-linked hydrophillic polymers. The polymers may differ in their chemical nature but they share the property of being capable of absorbing and retaining even under moderate pressure amounts of aqueous fluids equivalent to many times their own weight. For example superabsorbents can typically absorb up to 100 times their own weight or even more of distilled water.

Superabsorbents have been suggested for use in many different industrial applications where advantage can be taken of their water absorbing and/or retaining properties and examples include agriculture, the building industry, the production of alkaline batteries and filters. However the primary field of application for superabsorbents is in the production of hygienic and/or sanitary products such as disposable sanitary napkins and disposable diapers either for children or for incontinent adults. In such hygienic and/or sanitary products, superabsorbents are used, generally in combination with cellulose fibres, to absorb body fluids such as menses or urine. However, the absorbent capacity of superabsorbents for body fluids is dramatically lower than for deionised water. It is generally believed that this effect results from the electrolyte content of body fluids and the effect is often referred to as "salt poisoning".

The water absorption and water retention characteristics of superabsorbents are due to the presence in the polymer structure of ionisable functional groups. These groups may be carboxyl groups, a high proportion of which are in the salt form when the polymer is dry but which undergo dissociation and solvation upon contact with water. In the dissociated state, the polymer chain will have a series of functional groups attached to it which groups have the same electric charge and thus repel one another. This leads to expansion of the polymer structure which, in turn, permits further absorption of water molecules although this expansion is subject to the constraints provided by the cross-links in the polymer structure which must be sufficient to prevent dissolution of the polymer. It is assumed that the presence of a significant concentration of electrolytes in the water interferes with dissociation of the functional groups and leads to the "salt poisoning" effect. Although most commercial superabsorbents are anionic, it is equally possible to make cationic superabsorbents with the functional groups being, for example, quaternary ammonium groups. Such materials also need to be in salt form to act as superabsorbents and their performance is also affected by the salt-poisoning effect.

EP-A-0161762 relates to partially cross-linked copolymers of at least one diallylic quaternary ammonium salt, preferably a diallyldialkylammonium halide. The polymers are prepared by inverse suspension polymerisation with an oil phase as the continuous phase and an aqueous phase as the discontinuous phase. The polymers which are produced directly in salt form are said to be water-swellable polymers whose water absorbtion properties are not significantly diminished when used to absorb saline solutions. However, the specific example in EP-A-0161762 relates to a material which has, on the basis of the results reported in the specification, a water absorption capacity in 0.9% by weight NaCl solution only about 20% of its absorption capacity in deionised water.

It is an object of the present invention to provide a cationic water absorbent polymer with improved water absorption properties and in particular water absorption properties in respect of saline solution.

According to one aspect, the present invention provides a water-swellable, water-insoluble polymer comprising units derived from a diallylic quaternary ammonium salt monomer, cross-linked by a suitable polyfunctional vinyl compound, characterised in that the polymer has been produced by cationic polymerisation in an aqueous phase using a free radical catalyst.

According to another aspect, the present invention provides a water-swellable, water-insoluble polymer comprising units derived from a diallylic quaternary ammonium salt monomer cross-linked by a suitable polyfunctional vinyl compound, characterised in that at least a substantial proportion of the functional groups are in basic form.

According to a still further aspect, the present invention provides a process for the production of a waterswellable, water-insoluble polymer which comprises polymerising a diallylic quaternary ammonium salt monomer and a suitable polyfunctional vinyl compound as cross-linking agent by cationic polymerisation in an aqueous phase using a free radical catalyst.

It has surprisingly been found according to the present invention that polymerising a diallylic quaternary ammonium salt monomer together with a suitable cross-linking agent by cationic polymerisation in an aqueous phase produces a water-swellable, water-insoluble polymer having significantly improved properties as compared to the polymers of EP-A-0161762. More particularly, the polymer produced by cationic polymerisation in the aqueous phase shows improved water absorption in deionised water and/or in saline solution.

As already noted, the polymers of EP-A-0161762 are produced by inverse suspension polymerisation. It is to be expected that the different polymerisation methods as between EP-A-0161762 and the present invention, i.e. inverse suspension polymerisation as opposed to cationic polymerisation in the aqueous phase, will lead to differences in the final product. These differences may reside, for example, in uniformity of cross-linking and uniformity of molecular weight. Whilst these differences cannot be identified and defined, the differences in properties between the products and in particular the improved properties of the product according to the present invention, demonstrate that the products themselves are different.

The present invention is applicable to any diallylic quaternary ammonium salt monomer which is suitable for the production of water-swellable polymers. Essentially the monomers have the formula

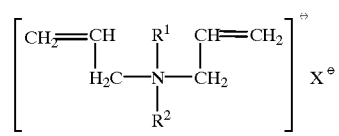

wherein $R^1$ and $R^2$, which may be the same or different, are each organic radicals which do not adversely affect the properties of the polymer and X is a suitable anion.

Preferably $R^1$ and $R^2$ are each independently an optionally substituted saturated hydrocarbon group or aryl group. For example the saturated hydrocarbon group may be an alkyl group which may be straight or branched chain or cyclic. The aryl group also includes arylalkyl groups. Preferably the groups $R^1$ and $R^2$ have from 1 to 20 carbon atoms, more preferably from 1 to 6 carbon atoms. The saturated hydrocarbon group or the aryl group may be substituted by one or more suitable substituents selected from carboxyl, ester, hydroxyl, ether, sulphate, sulphonate, primary, secondary or tertiary amines or quaternary ammonium groups. In the case of ester (—$CO_2R$) and ether (—O—R) the R group is a hydrocarbon radical having from 1 to 20, preferably from 1 to 6 carbon atoms, more preferably the R group is methyl. In the case of aryl groups, suitable substituents include saturated hydrocarbon groups as defined above. The preferred groups for $R^1$ and $R^2$ are methyl groups.

X may be any suitable anion which may be inorganic or organic. Suitable inorganic anions include halide (in particular fluoride, chloride, bromide and iodide), nitrate, phosphate, nitrite, carbonate, bicarbonate, borate, sulphate and hydroxide. Suitable organic anions include carboxylate such as acetate citrate, salicilate and propionate.

Preferably the anion is a chloride or hydroxide ion.

Preferred monomers are diallyl dimethyl ammonium chloride and dimethyl diallyl ammonium hydroxide.

A particularly preferred diallylic quaternary ammonium salt monomer is dimethyldiallyl ammonium chloride.

Polymerisation of a diallylic quaternary ammonium salt monomer in the presence of a free-radical initiator produces a linear polymer as follows:

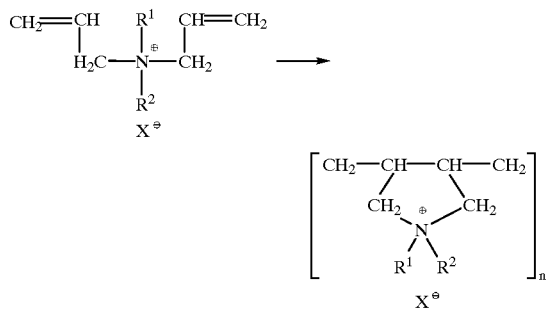

where n is the number of monomer units. In order to ensure that the polymer remains insoluble on swelling with water, it is necessary to introduce a sufficient degree of crosslinking into the polymer by including a suitable crosslinking agent in the polymerisation reaction.

Suitable cross-linking agents are generally vinyl compounds with two or more polymerisable double bonds in the molecule. Specific examples of cross-linking agents include divinyl benzene and N,N-methylene bisacrylamide. The crosslinker should be employed in a sufficient quantity such that the absorbent gelling material (AGM) produced is insoluable when it is in contact with aqueous solutions, however the crosslinker must not be used in such quantities that it interferes with the ability of the AGM to absorb aqueous solutions. The amount of crosslinker used in mole % relative to the number of moles of monomer is in the range of from 0.01 to 20% and preferably in the range of from 0.05 to 5%.

The cationic polymerisation according to the invention takes place in aqueous medium in the presence of a suitable free-radical initiator. Any free radical initiator of the type conventionally used for cationic polymerisation can be used including organic peroxides, such as hydrogen peroxide, persulphates, such as ammonium persulphate and azo compounds, such 2,2-azobis(2-methyl propionamidine) dihydrochloride. Preferred free radical initiators include azo compounds and particularly azobisisobutyronitrile ("AZBN").

The process for polymerization may be conducted as follows:

The following solutions were prepared:
a) An aqueous 60% solution of monomer.
b) An approximate 230 g/l solution of crosslinker in distilled water.
c) An approximate 60 g/l solution of a free radical initiator in distilled water.

a) was disareated with, for example, a vacuum pump. Thereafter b) and c) were added to a) with continuous stirring. The mixture was heating to approximately 60° C. A solid product formed after approximately four hours. The product was cut to obtain smaller pieces and swelled by adding approximately 4 liters of distilled water thereto. After approximately 2 hours the swelled gel was filtered using, for example, a nonwoven fabric tissue filter. The gel was dried, for example, in a ventilated air oven at approximately 60° C. for approximately 10 hours resulting in approximately 100 g of dried product.

The product formed may be converted into basic form by swelling the product in distilled water, adding an alkali solution for example NaOH with continuous stirring, after approximately 1 hour the gel was filtered. Treatment with hydroxide and filtering was repeated until no further chloride ions were present in the washing waters; this may be measured by precipitation titration using silver nitrate (AgN03). The gel was washed with distilled water until the washing water had a pH of 7. The product is dried, for example, in a ventilated air oven.

Apart from differences in terms of the nature of the product, the process according to the present invention which involves solution polymerisation in aqueous medium has advantages over the inverse suspension polymerisation process of EP-A-0161762 in terms of the process itself. In particular, solution polymerisation in aqueous medium requires addition of fewer components to the reaction medium, for example emulsifiers are not required, and this leads to less impurities in the final product. In addition the polymerisation proceeds better with a product of higher molecular weight being formed.

The process according to the present invention leads to a product which can be used as an absorbent for water or saline in either salt or basic form. The basic form of the polymer may be obtained from the salt form of the polymer by conversion with alkali as described previously.

In use in absorbing saline, for example in the form of salt containing liquids such as urine or menses, there are considerable advantages in using the polymer according to the invention in basic form. In this case, at the same time as absorbing the liquid, the polymer also has a desalting effect on the liquid by virtue of the conversion of the polymer into the salt form. As the polymer according to the invention is a strong ion exchanger the polymer will spontaneously convert to the salt form of the polymer when in contact with saline solution.

The absorbent according to the present invention is particularly suitable for use in applications where it is desired to absorb salt containing aqueous liquids. Examples of such liquids include in particular menses and urine and the absorbent material can be used as the filling in catemenials and diapers generally in admixture with a fibrous absorbent such as cellulose fluff. The absorbent according to the present invention in base form can also be used in conjunction with an anionic superabsorbent in free acid form or a cation exchanger in acid form as described in our copending patent applications nos . . . (internal reference DR 24) and . . . (internal reference DR 26) respectively.

The invention is illustrated further by the following examples.

EXAMPLE 1

10 g of a 60% aqueous solution of diallyldimethyl ammonium chloride was mixed with 0.0172 g of N,N-methylene-bisacrylamide (cross-linking agent) with continuous stirring in a 150 ml vacuum flask. Nitrogen gas was bubbled into the reaction vessel for 15 minutes, after which 0.015 g of ammonium persulphate (free radical initiator) was added and the reaction mixture heated to 70° C. and maintained at that temperature for 3 hours stirring was continued with a magnetic bar until the bar is prevented from moving. As the polymer forms the solution gels and becomes a solid.

A large volume of deionised water was then added to the polymer and the polymer was allowed to swell for 24 hours, creating a swelled gel. The swelled polymer was then dried in a forced convection oven for 10 hours at 100° C. and the dried polymer mechanically blended to a powder. The resultant polymer is in salt form. The base form is obtained by treatment of the polymer in Cl form with alkali (NaOH 0.01 m) as follows:

20 g of polymer were placed in a 10 liter beaker and 4 liters of distilled water were added thereto. After the polymer has swelled 500 ml of NaOH were added with continuous stirring. After 1 hour the gel was filtered with a nonwoven fabric tissue filter. The NaOH treatment and filtration steps were repeated until no further chloride ion were present in the washing waters (by agentometic titration). The gel was then washed with distilled water until the waters are neutral (pH 7). The gel was dried in a ventilated oven at 60° C. to obtain the product.

The dried powder was tested for absorption of deionised water and 0.9% sodium chloride solution according to the method described below in Example 2 which is equivalent to that reported in EP-A-0161762.

The results were as follows:

|  | Absorption g/g (Tea-bag test) | |
| --- | --- | --- |
|  | Deionised Water | 0.9% NaCl |
| Polymer of Example 1 in salt form | 320 | 55 |
| Polymer of Example 1 in base form | 350 | 48 |
| Polymer of EP-A-0161762 | 160 | 31 |

The above results show that the polymer according to the invention shows a surprisingly greater absorption that the polymer of EP-A-0161762 both in the case of deionised water and 0.9% NaCl solution. The polymer according to the invention can absorb liquid irrespective of whether it is in the salt or base form.

EXAMPLE 2

Preparation of Fai 7 OH 133 g of 60% aqueous solution of dimethyl diallyl ammonium chloride (DMAC available from fluka) were weighed into a 250 ml flask.

0.2 g of bisacrylamide (BAC available from fluka) were weighed separately into a 5 ml test tube and were dissolved using 2 ml of distilled water.

0.12 g of ammonium persulfate (free radical initiator) were dissolved in a 5 ml test tube using 2 ml of distilled water.

The monomer solution was disareated by vacuum using a vacuum pump.

Thereafter under continuous stirring the crosslinker solution and free radical intiator were added to the monomer solution, the temperature was adjusted to 60° C. by placing the flask in a thermostatic bath for four hours.

The solid product formed was cut using a spatula and transferred in 5 liter beaker containing 4l of distilled water, after two hours the swelled gel was filtered by a nonwoven tissue fabric filter. The gel was dried in a ventilated oven at 60° C. for 12 hours. 60 g of dried polymer was collected and called Fai 7 Cl. 20 g of Fai 7 Cl was placed in a 10 liter beaker and swelled by adding 4l of distilled water, under continuous stirring. When the polymer has swelled (after 2 hours) 500 ml of 0.01 M NaOH solution was added and after 30 minutes the gel was filtered using a nonwoven fabric tissue filter. These operations (alkalinization and filtration) were repeated until there were no chloride ions in the washing waters (chloride ions may be checked by $AgNO_3$ reaction). At this point the gel was washed with distilled water until there was no further evidence of the basic reaction of the washing waters.

At the end the gel was dried in an ventilated oven at 60° C. for 12 hours 10 g of dried polymer was collected and was called Fai 7 OH.

The dried powder was tested for absorbence in deionized water and in a 1% NaCl solution according to the tea bag test as follows:

0.3 g of AGM was weighed into a tea bag envelope and allowed to swell in a 250 ml beaker containing 150 ml of NaCl 1% solution (or deionized water) for 1 hour. Thereafter the beaker was removed and the envelope remained suspended for 10 minutes and unabsorbed water drained therefrom. The envelope containing the swelled AGM was then weighed and absorbency was calculated as follows:

$$A=(Wwet-Wdry)/G$$

where:

A=absorbency Wwet=envelope containing the wet AGM in g Wdry=envelope containing the dry AGM in g G=dry AGM for the test in g.

|  | Absorbence g/g tea bag test | |
| --- | --- | --- |
|  | Deionized water | NaCl 1% |
| Fai 7 OH | 351 | 55 |
| Fai 7 Cl | 340 | 54 |

What is claimed is:

1. A water-swellable, water-insoluble polymer comprising units derived from a diallylic quaternary ammonium salt monomer, cross-linked by a suitable polyfunctional vinyl compound, characterised in that the polymer has been produced by a single phase polymerization in an aqueous medium using a free radical catalyst.

2. A water-swellable, water-insoluble polymer comprising units derived from a diallylic quaternary ammonium salt monomer cross-linked by a suitable polyfunctional vinyl compound, characterised in that at least a substantial proportion of the functional groups are in basic form.

3. A water swellable, water insoluble polymer as claimed in claim 2 wherein the monomer has the formula

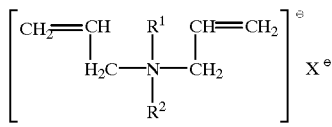

wherein $R^1$ and $R^2$, which may be the same or different, are each organic radicals which do not adversely affect the properties of the polymer and X is a suitable anion.

4. A water swellable, water insoluble polymer as claimed in claim 3 wherein $R^1$ and $R^2$ are each independently an optionally substituted saturated hydrocarbon group or aryl group.

5. A water swellable, water insoluble polymer as claimed in claim 4 wherein the saturated hydrocarbon group or the aryl group may be substituted by one or more suitable substituents selected from carboxyl, ester, hydroxyl, ether, sulphate, sulplonate, primary, secondary or tertiary amines or quaternary ammonium groups.

6. A water swellable, water insoluble polymer as claimed in claim 5 wherein the groups $R^1$ and $R^2$ and the R groups in the ester and ether substituents have from 1 to 20 carbon atoms.

7. A water swellable, water insoluble polymer as claimed in claim 6 wherein the $R^1$, $R^2$ and R groups are methyl.

8. A water swellable, water insoluble polymer as claimed in claim 3 wherein X is a halide, nitrate, phosphate, nitrite, carbonate, bicarbonate, borate, sulphate or a carboxylate anion.

9. A water swellable, water insoluble polymer as claimed in claim 8 wherein X is a chloride or hydroxide anion.

10. A water swellable, water insoluble polymer as claimed in claim 3 wherein the monomer is dimethyl diallyl ammonium chloride or dimethyl diallyl ammonium hydroxide.

11. A water swellable, water insoluble polymer as claimed in claim 10 wherein the monomer is dimethyl diallyl ammonium chloride.

12. A process for the production of a water-swellable, water-insoluble polymer which comprises polymerising a diallylic quaternary ammonium salt monomer and a suitable polyfunctional vinyl compound as cross-linking agent by a single phase polymerization in an aqueous medium using a free radical catalyst.

13. A process as claimed in claim 12 wherein the crosslinking agent is a vinyl compound having two or more polymerizable bonds in the molecule.

14. A process as claimed in claim 13 wherein the crosslinking agent is divinyl benzyl or N,N-methyl bisacrylamide.

15. A process as claimed in claim 12 wherein the quantity of crosslinker in mole % relative to the number of moles of monomer is in the range of from 0.01 to 20%.

16. A process as claimed in claim 12 wherein the free radical initiator is an organic peroxide, a persulphate or an azo compound.

17. A process as claimed in claim 16 wherein the free radical initiator is hydrogen peroxide, ammonium persulphate or 2,2-azo (2-methyl propionamidine) dihydrochloride.

18. A process as claimed in claim 17 wherein the free radical initiator is 2,2-azo (2-methyl propionamidine) dihydrochloride.

19. A method of using the polymer as claimed in claim 2 for the absorption of electrolyte containing aqueous liquids, the method comprising the step of introducing the electrolyte containing aqueous liquids to the polymer.

20. The method according to claim 19 wherein the liquid is menses or urine.

21. The method according to claim 19 wherein the polymer is in base form and is used in conjunction with an anionic superabsorbent in free acid form or a cation exchanger in acid form.

22. A water swellable, water insoluble polymer as claim in claim 6 wherein the groups $R^1$ and $R^2$ and the R groups in the ester and ether substituents have from 1 to 6 carbon atoms.

23. A process as claimed in claim 15 wherein the quantity of crosslinker in mole % relative to the number of moles of monomer is in the range of from 0.05 to 5%.

* * * * *

UNITED STATES PATENT AND TRADEMARK OFFICE
CERTIFICATE OF CORRECTION

PATENT NO. : 6,084,045
DATED : July 4, 2000
INVENTOR(S) : Fornasari et al.

It is certified that error appears in the above-identified patent and that said Letters Patent is hereby corrected as shown below:

Title page,
Item [30], Foreign Application Priority Data, please delete "TO94A0888" and insert therefor -- TO94A000888 --.

Column 4,
Lines 64-65, please delete "applications nos ... (internal reference DR 24) and ... (internal reference DR26 respectively." and insert therefor -- application serial nos. 08/849,607 and 08/836,298 --.

Column 7,
Line 20, please delete "sulplonate" and insert therefor -- sulphonate --.

Column 8,
Line 34, please delete "claim" and insert therefor -- claimed --.

Signed and Sealed this

Thirteenth Day of July, 2004

JON W. DUDAS
*Acting Director of the United States Patent and Trademark Office*